(12) United States Patent
Hester, II et al.

(10) Patent No.: US 8,580,767 B2
(45) Date of Patent: Nov. 12, 2013

(54) OXAZOLIDINONE CONTAINING DIMER COMPOUNDS, COMPOSITIONS AND METHODS TO MAKE AND USE

(75) Inventors: D. Keith Hester, II, Delmar, NY (US); Robert J. Duguid, Glenmont, NY (US); John Finn, Encinitas, CA (US)

(73) Assignee: Trius Therapeutics, Inc., San Diego, CA (US)

( * ) Notice: Subject to any disclaimer, the term of this patent is extended or adjusted under 35 U.S.C. 154(b) by 339 days.

(21) Appl. No.: 12/787,293

(22) Filed: May 25, 2010

(65) Prior Publication Data

US 2010/0305069 A1 Dec. 2, 2010

Related U.S. Application Data

(60) Provisional application No. 61/181,955, filed on May 28, 2009.

(51) Int. Cl.
    *A01N 57/00* (2006.01)
    *A61K 31/675* (2006.01)
    *C07F 9/06* (2006.01)
    *C07F 9/28* (2006.01)

(52) U.S. Cl.
    USPC .............................................. 514/89; 546/22

(58) Field of Classification Search
    USPC ............................................ 514/89; 546/22
    See application file for complete search history.

(56) References Cited

U.S. PATENT DOCUMENTS

| | | | |
|---|---|---|---|
| 4,128,654 A | 12/1978 | Fugitt et al. |
| 4,250,318 A | 2/1981 | Dostert et al. |
| 4,340,606 A | 7/1982 | Fugitt et al. |
| 4,461,773 A | 7/1984 | Gregory |
| 4,476,136 A | 10/1984 | Dostert et al. |
| 4,948,801 A | 8/1990 | Carlson et al. |
| 5,523,403 A | 6/1996 | Barbachyn |
| 5,565,571 A | 10/1996 | Barbachyn |
| 5,652,238 A | 7/1997 | Brickner et al. |
| 5,688,792 A | 11/1997 | Barbachyn et al. |
| 6,365,751 B1 | 4/2002 | Gravestock |
| 6,627,646 B2 | 9/2003 | Bakale et al. |
| 6,689,779 B2 | 2/2004 | Lee et al. |
| 7,129,259 B2 | 10/2006 | Chen et al. |
| 7,141,583 B2 | 11/2006 | Gravestock et al. |
| 7,144,911 B2 | 12/2006 | Flynn et al. |
| 7,202,257 B2 | 4/2007 | Flynn et al. |
| 7,396,847 B2 | 7/2008 | Gravestock et al. |
| 7,462,633 B2 | 12/2008 | Fukuda |
| 7,473,699 B2 | 1/2009 | Gravestock et al. |
| 7,498,350 B2 | 3/2009 | Gravestock et al. |
| 7,816,379 B2 | 10/2010 | Rhee et al. |
| 2002/0115669 A1 | 8/2002 | Wiedeman et al. |
| 2003/0166620 A1 | 9/2003 | Lee et al. |
| 2004/0180906 A1 | 9/2004 | Flynn et al. |
| 2005/0038092 A1 | 2/2005 | Fukuda |
| 2005/0107435 A1 | 5/2005 | Gravestock et al. |
| 2005/0288286 A1 | 12/2005 | Flynn et al. |
| 2006/0116386 A1 | 6/2006 | Gravestock |
| 2006/0116400 A1 | 6/2006 | Carcanague et al. |
| 2006/0270637 A1 | 11/2006 | Gravestock et al. |
| 2007/0155798 A1 | 7/2007 | Rhee et al. |
| 2007/0185132 A1 | 8/2007 | Fukuda |
| 2007/0191336 A1 | 8/2007 | Flynn et al. |
| 2007/0203187 A1 | 8/2007 | Fukuda |
| 2007/0208062 A1 | 9/2007 | Carcanague et al. |
| 2008/0021012 A1 | 1/2008 | Gravestock et al. |
| 2008/0021071 A1 | 1/2008 | Gravestock et al. |
| 2008/0064689 A1 | 3/2008 | Carcanague et al. |
| 2009/0018123 A1 | 1/2009 | Sindkhedkar et al. |
| 2009/0192197 A1 | 7/2009 | Rhee et al. |
| 2010/0093669 A1 | 4/2010 | Simson et al. |
| 2010/0227839 A1 | 9/2010 | Reichenbacher et al. |

FOREIGN PATENT DOCUMENTS

| | | |
|---|---|---|
| AU | 2004299413 | 7/2009 |
| AU | 2009200606 | 4/2011 |
| CA | 2 549 062 | 7/2011 |
| CN | 101982468 A | 3/2011 |
| EP | 0312000 | 4/1989 |

(Continued)

OTHER PUBLICATIONS

Dorwald F. A. Side Reactions in Organic Synthesis, 2005, Wiley: VCH, Weinheim p. IX of Preface.*

Chinese, First Office Action, re Application No. 201010508824.1, dated Jul. 6, 2011.

European Patent Office Communication re Correction of deficiencies noted in the written opinion and amended. Re EPO App. No. 09749235.9, dated Jun. 24, 2011.

Espinoza-Gonzalez, et al., "Efficacy of DA-7218, a new oxazolidinone prodrug, in the treatment of experimental actinomycetoma produced by Nocardia brasiliensis", Molecules (Basel, Switzerland) LNKD-PUBMED: 18259127, vol. 13, No. 1, pp. 31-40 (2008).

(Continued)

*Primary Examiner* — Sreeni Padmanabhan
*Assistant Examiner* — Uma Ramachandran
(74) *Attorney, Agent, or Firm* — Knobbe, Martens, Olson & Bear LLP (57) ABSTRACT

Dosage forms or pharmaceutical compositions comprise a compound having the structure of Formula IV:

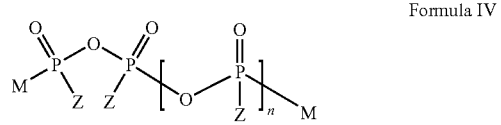

Formula IV wherein n is a non-negative integer; wherein each Z is an oxazolidinone-containing moiety having antibiotic activity in vivo upon cleaving, wherein M is independently $OR_1$ or $NR_1R_2$; wherein $R_1$ and $R_2$ are independently selected from the group consisting of H, an optionally-substituted hydrocarbyl residue or a pharmaceutically acceptable cation; wherein the compound in the dosage form or a pharmaceutical composition is present in an amount effective for treating or preventing an antibacterial infection in a mammalian subject. Methods of preparing and using these dosage forms or pharmaceutical compositions are also disclosed.

14 Claims, 3 Drawing Sheets

(56) References Cited

FOREIGN PATENT DOCUMENTS

| | | |
|---|---|---|
| EP | 0 352 781 | 1/1990 |
| EP | 1 699 784 | 9/2006 |
| EP | 2 305 657 | 4/2011 |
| EP | 2435051 | 4/2012 |
| IN | 236862 | 11/2009 |
| JP | A-S57-99576 | 6/1982 |
| KR | 11-71107 | 6/2011 |
| NZ | 547928 | 9/2009 |
| NZ | 575842 | 2/2011 |
| WO | WO 93/09103 | 5/1993 |
| WO | WO 93/23384 | 11/1993 |
| WO | WO 95/07271 | 3/1995 |
| WO | WO 95/14684 | 6/1995 |
| WO | WO 01/94342 | 12/2001 |
| WO | WO 02/081470 | 10/2002 |
| WO | WO 03/022824 | 3/2003 |
| WO | WO 03/035648 | 5/2003 |
| WO | WO 03/047358 | 6/2003 |
| WO | WO 03/072575 | 9/2003 |
| WO | WO 03/072576 | 9/2003 |
| WO | WO 2004/048350 | 6/2004 |
| WO | WO 2004/083205 | 9/2004 |
| WO | WO 2005/005398 | 1/2005 |
| WO | WO 2005/051933 | 6/2005 |
| WO | WO 2005/058886 | 6/2005 |
| WO | WO 2005/058886 A1 | 6/2005 |
| WO | WO 2005/116017 | 12/2005 |
| WO | WO 2006/038100 | 4/2006 |
| WO | WO 2007/023507 | 3/2007 |
| WO | WO 2007/138381 | 12/2007 |
| WO | WO 2010/042887 | 4/2010 |
| WO | WO 2010/091131 | 8/2010 |
| WO | WO 2010/138649 | 12/2010 |

OTHER PUBLICATIONS

International Preliminary Report on Patentability re App. No. PCT/US2010/023122 dated Aug. 9, 2011.
New Zealand Office Action re App. No. 575842, dated Jul. 1, 2011.
Australian Examiner's First Report, dated Oct. 12, 2010, re App. No. 2009200606.
Bae et al., "High-Performance liquid chromatographic analysis of DA-7867, a new oxazolidinone, in human plasma and urine and in rat tissue homogenates", In Journal of Chromatography B, Sep. 5, 2003, 794, p. 397-403.
Bae, Soo K., et al. 2007 "Pharmacokinetics of DA-7218, a New Oxazolidinone, and Its Active Metabolite, DA-7157, After Intravenous and Oral Administration of DA-7218 and DA-7157 to Rats", Journal of Pharmacy and Pharmacology 59:955-963.
CA Notice of Allowance re App. No. 2,549,062, dated Apr. 7, 2011.
CA Office Action re App. No. 2,549,062 dated Aug. 21, 2008.
CA Office Action re App. No. 2,549,062 dated Jan. 12, 2011.
CA Office Action re App. No. 2,549,062 dated Mar. 30, 2009.
CN Decision of Rejection re App. No. CN 200480037612.2 dated Jun. 26, 2009.
CN Office Action re App. No. CN 200480037612.2 dated Jan. 9, 2009.
EP Extended Search Report re EP App. No. 10 18 3967, dated Mar. 25, 2011.
EPO Examination Report re App. No. EP 04 80 8458 dated Apr. 30, 2010.
EPO Examination Report re App. No. EP 04 80 8458 dated Aug. 10, 2009.
EPO Supplemental Search Report re App. No. EP 04 80 8458 dated Jul. 24, 2008.
Hiroshi, Nagase ed. Medicinal Chemistry, Technomics, Sep. 25, 1999, The Second Volume, pp. 368-382.
International Partial Search Report re App. No. PCT/US2009/060267, dated Jan. 14, 2010.
International Preliminary Report on Patentability and Written Report, re PCT/US2009/060267 mailed on Apr. 21, 2011.
International Preliminary Report on Patentability for PCT/KR2004/003327 dated Jan. 9, 2006.
International Search Report and Written Opinion re App. No. PCT/US2009/060267, dated May 7, 2010.
International Search Report and Written Opinion re App. No. PCT/US2010/023122 dated Jul. 16, 2010.
International Search Report and Written Opinion re App. No. PCT/US2010/036283 dated Aug. 6, 2010.
International Search Report for PCT/KR2004/003327 dated Mar. 24, 2005.
International Search Report issued in International Application No. PCT/GB 03/05091 on Aug. 18, 2004.
J. Med. Chem. 32, 1673 (1989).
J. Med. Chem. 33, 2569 (1990).
Japanese Office Action re JP App. No. 2006-545238, dated Sep. 21, 2010.
Mexico Office Action re App. No. PA/a/2006/006955, dated Dec. 10, 2010.
Miyaura, et al.: "Palladium-Catalyzed Cross-Coupling Reactions of Organoboron Compounds", Chemical Reviews, ACS, Washington, DC, US, vol. 95, No. 7, Jan. 1, 1995, pp. 2457-2483.
NZ Examination Report re App. No. 575842 dated Sep. 23, 2010.
NZ Examination Report re App. No. 575842 dated Mar. 31, 2009.
NZ Examination Report re NZ Application No. 589161, dated Nov. 30, 2010.
NZ Office Action re App. No. 575842 dated Jan. 19, 2011.
NZ Office Action re App. No. 575842 dated Jul. 15, 2010.
Prado-Prado, Francisco, J., et al. 2007 "Unified QSAR Approach to Antimicrobials. Part 2: Predicting Activity Against More Than 90 Different Species in Order to Halt Antibacterial Resistance", Bioorganic & Medicinal Chemistry, 15:897-902.
Response to Office Action in Japanese Application No. 2006-545238 dated Apr. 4, 2011.
Rondestvedt, Christian, S., Jr., et al. 1955. "Unsaturated sulfonic acids. V", Journal of the American Chemical Society, 77:6532-6540.
Supplementary European Search Report dated Jul. 31, 2008.
Tetrahedron, vol. 45 No. 5 pp. 1323-1326, 1989 "Chiral Synthesis of DUP 721, A New Antibacterial AGENT1, Chia-Lin J. Wang, Walter A. Gregory, And Mark A. Wuonola E.I. Du Pont De Nemours And Company, Inc., Medical Products Department Pharh4aceutical Research And Development Division Experimental Station".
Vera-Cabrera, Lucio, et al. 2006 "In Vitro Activities of DA-7157 and DA-7218 Against Mycobacterium Tuberculosis and Nocardia Brasiliensis", Antimicrobial Agents and Chemotherapy 50:3170-3172.
Vera-Cabrera, Lucio, et al. 2006 "In Vitro Activities of the Novel Oxazolidinones DA-7867 and DA-7157 Against Rapidly and Slowly Growing Mycobacteria", Antimicrobial Agents and Chemotherapy 50:4027-4029.
Examination Report in New Zealand Application No. 596602 dated Sep. 21, 2012.
Office Action in U.S. Appl. No. 12/577,089 dated Jun. 4, 2012.
Office Action in U.S. Appl. No. 12/211,655 mailed Jul. 16, 2012.
Petition Decision in U.S. Appl. No. 12/577,089 mailed Sep. 7, 2012.
Petition Decision in U.S. Appl. No. 12/699,864 mailed Sep. 10, 2012.
U.S. Pharmacopia #23, National Formulary #18, 1995, 1843-1844.
Vera-Cabrera, et al, "In Vitro Activities of DA-7157 and DA7218 against Mycobacterium tuberculosis and Nocardia brasiliensis", Antimicrobial Agents and Chemotherapy, vol. 50, No. 9, pp. 3170-3172 (2006).
Brittan ed., Polymorphism in Pharmaceutical Science, NY: Marcel Dekker, Inc. 1999, 1-2, 183-226; 235-238.
Rouhi et al., The Right Stuff: From research and development to the clinic, getting drug crystals right is full of pitfalls, Chemical & Engineering News, Feb. 2003, 32-35.
Office Action in Vietnam Application No. 1-2011-02242, dated Mar. 7, 2012.
Office Action in Chinese Application No. 201010508824.1, dated Jul. 6, 2011.
CMU Pharmaceutical Polymorphism, Internet, p. 1-3 (2002) (printout Apr. 3, 2008).
Office Action issued in Columbia Application No. 11-097215, dated Oct. 13, 2011.

(56) References Cited

OTHER PUBLICATIONS

Concise Encyclopedia Chemistry, NY: Walter de Gruyter, 1993, 872-873.
Doelker, English Translation of Ann. Pharm. Fr., 2002, 60: 161-176, pp. 1-39.
Doelker, English Translation of S.T.P. Pratiques (1999), 9(5), 399-409—pp. 1033.
Office Action in Dominican Republic Application No. P2011-0251 dated Jan. 18, 2012.
Dorwald, Side Reactions in Organic Synthesis, 2005, Wiley: VCH Weinheim Preface, pp. 1-15 & Chapter 8, pp. 279-308.
Notice of Opposition issued in Ecuador Application No. SP-11-11285 dated Mar. 9, 2012.
EPO Communication re Correction of deficiencies noted in the written opinion and amended in EPO App. No. 09749235.9, dated Jun. 24, 2011.
Espinoza-Gonzalez, et al.: "Efficacy of DA-7218, a new oxazolidinone prodrug, in the treatment of experimental actinomycetoma produced by Nocardia brasiliensis", Molecules (Basel, Switzerland) 2008 LNKD-PUBMED: 18259127, vol. 13, No. 1, 2008, pp. 31-40.
Ettmayer, et al.: "Lessons Learned from Marketing and Investigational Prodrugs", J. Med. Chem., (2004), 47(10): 2393-2404.
European Examination Report issued in EP Application No. 10 183 967.8, dated Oct. 24, 2011.
Office Action in European Application No. 10703403.5, dated Jun. 11, 2012.
International Written Opinion re App. No. PCT/US2010/023122 dated Aug. 9, 2011.
Jain et al., Polymorphism in Pharmacy, Indian Drugs, 1986, 23(6), 315-329.
Muzaffar Muzaffar et al., Polymorphism and Drug Availability, J. of Pharm (Lahore), 1979, 1(1), 59-66.
Office Action issued New Zealand Application No. 575842, dated Jul. 1, 2011.
Otuska et al., Effect of Polymorphic forms of bulk powders on pharmaceutical properties of carbamazepine granules, Chem. Pharm. Bull., 47(6) 852-856 (1999).
Restriction Requirement issued in U.S. Appl. No. 12/577,089 dated Jun. 4, 2012.
Rowland et al., Clinical Pharmacokinetics Concepts and Applications, 1995, p. 123.
Silverman, The Organic Chemistry of Drug Design and Drug Action, NY: Academic Press, 1993, 72-76.
Singahal et al., Drug Polymorphism and dosage form design: a practical perspective, Advanced Drug Delivery Reviews 56, p. 335-347 (2004).
Stella, "Prodrugs as therapeutics", Expert Opin. Ther. Patents (2004), 14(3): 277-280.
Taday et al., Using terahertz pulse spectroscopy to study the crystalline structure of a drug: A case study of the polymorphs of ranitidine hydrochloride, J. of Pharm. Sci. 92(4), 2003, 831-838.
Testa, "Prodrug research: futile or fertile?" Biochemical Pharmacology, 68 (2004): 2393-2404.
Office Action issued in U.S. Appl. No. 12/699,864, dated May 17, 2012.
Office Action issued in U.S. Appl. No. 12/699,864, dated Feb. 10, 2012.
Office Action issued in U.S. Appl. No. 12/577,089, dated Mar. 19, 2012.
Office Action issued in U.S. Appl. No. 12/211,655, dated Feb. 10, 2012.
Office Action issued in U.S. Appl. No. 12/211,655, dated Nov. 3, 2011.
Ulicky, Comprehensive Dictionary of Physical Chemistry, NY: Prentice Hall, 1992, p. 21.
Wolff, et al.: "Metabolic Considerations in Prodrug Design", Burger's Medicinal Chemistry and Drug Discovery, 5th ed. vol. 1: Principles and Practice, pp. 949-982.

\* cited by examiner

FIGURE 1

Legend
- Concentration of Formula I generated when Formula IV is administered intravenously
- ◆ Concentration of Formula I generated when Formula IV is administered orally
- Concentration of Formula IV (M=imidazolium salt) when is administered intravenously

FIGURE 2

Legend
◈ Concentration of Formula III (M=OH) when is administered intravenously
■ Concentration of Formula I generated when Formula III (M=OH) is administered intravenously

FIGURE 3

OXAZOLIDINONE CONTAINING DIMER COMPOUNDS, COMPOSITIONS AND METHODS TO MAKE AND USE

CROSS-REFERENCE TO RELATED APPLICATIONS

This application claims priority to U.S. Prov. Appl. No. 61/181,955, which is incorporated herein by reference.

BACKGROUND OF THE INVENTION

1. Field of the Invention

The present disclosure relates to pharmaceutically-useful oxazolidinone-containing dimer compounds, compositions, and methods of making and using them for treatment and prophylaxis of diseases in mammals.

2. Description of the Related Art

Various oxazolidinone-containing compounds have been disclosed for use as antibiotics. For example, oxazolidinone-containing compounds have been described in U.S. patent application Ser. No. 10/596,412 (filed Dec. 17, 2004), and WO 04/048350, WO 03/022824 and WO 01/94342, which are incorporated herein by reference.

U.S. patent application Ser. No. 12/577,089 (filed Oct. 9, 2009) and U.S. patent application Ser. No. 12/699,864 (filed Feb. 3, 2010), which are assigned to the same assignee as in the present application, disclose phosphate dimer impurities made during the process of making of the compounds disclosed therein. Surprisingly, it has been found that compounds containing at least two phosphates binding two oxazolidinone-containing moieties, such as dimers of oxazolidinone-containing compounds have antibacterial activity similar to their dihydrogen monophosphate analog, but have an advantageously different release profile, as discussed below in more detail.

Bacterial infections pose a continuing medical problem because anti-bacterial drugs eventually engender resistance in the bacteria on which they are used. Consequently, a need exists for new drugs with efficacy against pathogenic bacteria for use in the therapy and prophylaxis of bacterial infections.

In particular, a need exists for anti-bacterial drugs with a variety of pharmacokinetic properties, such as drugs with a slow release profile, to enable physicians to employs different dosing schedules in therapeutic and prophylactic regimens in different clinical contexts, and also a variety of physico-chemical properties to facilitate preparation of different formulations of drugs with similar modes of action.

SUMMARY OF THE INVENTION

The dosage forms and compositions herein fulfill these needs.

In some aspects, a dosage form or a pharmaceutical composition comprises a therapeutically effective amount of compound having the structure of Formula IV:

Formula IV wherein n is a non-negative integer;
wherein each Z is an oxazolidinone-containing moiety having antibiotic activity in vivo upon cleaving,
wherein M is independently $OR_1$ or $NR_1R_2$;
wherein $R_1$ and $R_2$ are independently selected from the group consisting of H, an optionally-substituted hydrocarbyl residue that may contain one or more heteroatoms or a pharmaceutically acceptable cation.

In some embodiments, each Z of the dosage form or the pharmaceutical composition described herein, is wherein * is the point of attachment of Z to P;
wherein $R^1a$ and $R^1b$ are independently selected from H and F, provided that at least one of $R^1a$ and $R^1b$ is F, and
Het is an optionally-substituted five- or six-membered heterocycle comprising at least one N, O, or S atom.

In some embodiments, the compound in the dosage form or composition described herein has the structure Formula IV (n = 0)

wherein M is $OR_1$ and $R_1$ is a pharmaceutically-acceptable cation, such as a nitrogen-containing cation, e.g., an imidazolium cation. In some aspects of these embodiments, each Z is or The dosage form or the pharmaceutical composition may also further comprise a pharmaceutically acceptable carrier, diluent or excipient.

In some embodiments, each Z in the compound in the dosage form or the pharmaceutical composition has R stereochemistry, such as wherein each Z is Formula Ia In some embodiments, the compound in the dosage form or the pharmaceutical composition is In some aspects, Het is tetrazolyl.

Some embodiments also include methods of preparing the compound in the dosage form or pharmaceutical composition described herein, comprising the step of treating o the compound f the formula Z—H with a phosphorylating such as $POCl_3$.

Some embodiments include methods of preparing the compound described herein in the dosage form or pharmaceutical composition, comprising the step of treating with a dehydrating agent of the compound Z—P', wherein P' is a mono-or dihydrogen phosphate group.

Embodiments also include methods of and uses for treating a bacterial infection comprising administering the dosage form or the pharmaceutical composition described herein to a subject in need thereof.

These and other embodiments are described in greater detail below.

DETAILED DESCRIPTION OF THE PREFERRED EMBODIMENT

In some embodiments, the present disclosure describes new prodrug compounds having antibiotic activity and pharmaceutical compositions containing the compounds as well as methods of making and using them. In some embodiments, the compounds are prodrugs that are cleaved after administration to release an active oxazolidinone-containing metabolite, in vivo. In some embodiments, the compound has the structure of Formula IV:

Formula IV wherein n is a non-negative integer;

wherein Z is an oxazolidinone-containing moiety having antibiotic activity in vivo upon cleaving, wherein M is independently $OR_1$ or $NR_1R_2$;

wherein $R_1$ and $R_2$ are independently selected from the group consisting of H, an optionally-substituted hydrocarbyl residue or a pharmaceutically acceptable cation.

In some embodiments, the compound is in a pharmaceutical composition or a dosage form, wherein the pharmaceutical composition or dosage form provides an effective antibiotic-treating or -preventing amount of the compound.

In some embodiments, the oxazolidinone-containing moiety, Z, has the structure wherein * is the point of attachment of Z to P;

wherein $R^1a$ and $R^1b$ are independently selected from H and F, provided that at least one of $R^1a$ and $R^1b$ is F, and

Het is an optionally-substituted five- or six-membered heterocycle comprising at least one N, O, or S atom, such as tetrazolyl or oxadiazolyl.

In some aspects, R1a is F and R1b is H and Het is 2-methyltetrazol-5-yl. For example, in some embodiments Z is

In some aspects, the active metabolite results after in vivo cleaving of the Z moiety from the compounds described herein. For example, an active metabolite may have the following formula:

Formula I

In some embodiments, the active drug of Formula I is (5R)-3-[3-fluoro-4-[6-(2-methyl-2H-tetrazol-5-yl)-3-pyridinyl]phenyl]-5-(hydroxymethyl)-2-oxazolidinone, i.e., Formula Ia ("TR-700".)

These active compounds have been disclosed in WO 05/058886 and US Patent Publication No. 20070155798, while processes for making these and related compounds have been disclosed in U.S. patent application Ser. No. 12/577,089 (filed Oct. 9, 2009), and a crystalline form of the phosphate ester and related salts of the above compound has been disclosed in U.S. patent application Ser. No. 12/699,864 (filed Feb. 3, 2010). The latter two applications are assigned to the same assignee as in the present application. Each of the references cited herein is hereby incorporated by reference in its entirety.

Compounds of Formula IV may occur as an impurity, along with other impurities, during the phosphorylation of the active metabolite of an oxazolidinone-containing antibiotic (e.g., Formula I). Therefore, these "impurities" have not been contemplated for use as pharmaceutical drugs. As an illustration, phosphorylation of Formula I forms the phosphate dihydrogen monoester prodrug of Formula II Formula II wherein M is described herein, such as a compound with the following formula

Formula II (M = OH)

Likewise, in a similar illustration, phosphorylation of the compound of Formula Ia (TR-700) forms the phosphate dihydrogen monoester of Formula IIa, [(5R)-3-{3-fluoro-4-[6-(2-methyl-2H-tetrazol-5-yl)pyridin-3-yl]phenyl}-2-oxo-5-oxazolidinyl]methyl]phosphate,

Formula IIa (M = OH)

In addition, salts of Formula II such as the disodium salts of Formula IIa may also be formed such as Formula IIb below:

Formula IIb

(M = ONa) or "TR-701"

Examples of impurities that may result during such phosphorylation of an active metabolite of an oxazolidinone-containing antibiotic include compounds of Formula III ("bis" compounds),

Formula III such as the phosphate monohydrogen diester (when M=OH), wherein Z is and wherein is the point of attachment of Z to P.

The side products may also include Formula IV

Formula IV wherein n is a non-negative integer such as 0, 1, or 2. In some embodiments, n is 0 and has the following formula:

Formula IV (n = 0)

wherein Z is as defined above, such as, the diphosphate dihydrogen diester of Formula I (when M=OH).

In some embodiments, Formula IV is an acid or an acid derivative, such as a salt, ester, or amide. In some embodiments, M is independently $OR_1$ or $N_1Z_1R_2$; wherein $R_1$ and $R_2$ are independently selected from the group consisting of H, optionally-substituted hydrocarbyl residue that may contain one or more heteroatoms, a pharmaceutically-acceptable cation, and a positively charged nitrogen-containing ion. In some embodiments, the presence of M may not substantially destroy the antibiotic activity of the active metabolite of the compound of Formula IV. In some embodiments, however, the presence of M may alter the degree of antibiotic activity.

In some embodiments, an optional substituent on the hydrocarbyl residue mentioned above, likewise may not substantially destroy antibiotic activity of the active metabolite of the compound of Formula IV. In some embodiments, the substituent may alter the degree of antibiotic activity, however. Antibiotic activity may be measured by various methods known in the art, such as the mouse septicemia model as described in Example 5.

As used herein, "hydrocarbyl residue" refers to a residue which contains only carbon and hydrogen. The residue may be aliphatic or aromatic, straight-chain, cyclic, branched, saturated or unsaturated. The hydrocarbyl residue, when indicated, may contain heteroatoms over and above the carbon and hydrogen members of the substituent residue. Thus, when specifically noted as containing such heteroatoms, the hydrocarbyl residue may also contain carbonyl groups, amino groups, hydroxyl groups and the like, or contain heteroatoms within the "backbone" of the hydrocarbyl residue. In some embodiments, the hydrocarbyl residue has 1-20 C containing 0-5 heteroatoms selected from O, S and N.

As used herein, the term "alkyl," "alkenyl" and "alkynyl" include straight- and branched-chain and cyclic monovalent substituents. Examples include methyl, ethyl, isobutyl, cyclohexyl, cyclopentylethyl, 2-propenyl, 3-butynyl, and the like. Typically, the alkyl, alkenyl and alkynyl substituents contain 1-10 C (alkyl) or 2-10 C (alkenyl or alkynyl), such as 1-6 C (alkyl), 2-6 C (alkenyl or alkynyl) or 3-6 C cycloalkyl. Heteroalkyl, heteroalkenyl and heteroalkynyl are similarly defined but may contain 1-2 O, S or N heteroatoms or combinations thereof within the backbone residue.

As used herein, "acyl" encompasses the definitions of alkyl, alkenyl, alkynyl and the related hetero-forms which are coupled to an additional residue through a carbonyl group.

"Aromatic" moiety refers to a monocyclic or fused bicyclic moiety such as phenyl or naphthyl; "heteroaromatic" also refers to monocyclic or fused bicyclic ring systems containing one or more heteroatoms selected from O, S and N. The inclusion of a heteroatom permits inclusion of 5-membered rings as well as 6-membered rings. Thus, typical aromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl, tetrazolyl, oxadiazolyl and the like. Any monocyclic or fused ring bicyclic system which has the characteristics of aromaticity in terms of electron distribution throughout the ring system is included in this definition. Typically, the ring systems contain 5-12 ring member atoms.

Similarly, "arylalkyl" and "heteroarylalkyl" refer to aromatic and heteroaromatic systems which are coupled to another residue through a carbon chain, including substituted or unsubstituted, saturated or unsaturated, carbon chains, typically of 1-6 C. These carbon chains may also include a carbonyl group, thus making them able to provide substituents as an acyl moiety.

Optional substituents may be selected from the group consisting of optionally substituted alkyl, alkenyl, alkynyl, aryl, N-aryl, NH-aroyl, halo, OR, $NR_2$, SR, —OOCR, —NROCR, RCO, —COOR, —CONR$_2$, SO$_2$NR$_2$, CN, CF$_3$, and NO$_2$, wherein each R is independently H or alkyl (1-4 C).

In some embodiments where M=OR$_1$, R$_1$ may be a H or a metal cation such as an alkali metal cation or an alkaline earth metal cation. In some embodiments, the metal cation is sodium, calcium, potassium, magnesium, aluminum, zinc, or lithium cation.

In some embodiments where M=OR$_1$, R$_1$ may be a positively charged nitrogen-containing group that forms a salt with the negatively charged oxygen of Formula IV, such as ammonium and the quaternized or positively charged salts of imidazole, N-methylglucamine, choline, piperazine, tromethamine, diethylamine, 4-phenylcyclohexylamine, or benzathine. In this context "quaternized" refers to a nitrogen atom having four bonds and therefore having a net positive charge, such as nitrogen with four pendant groups or bonds, such as one with a double bond. In some embodiments, pendant groups may include one or more hydrogens. In some embodiments, M is O-imidazolium salt, that is, —O—

Pharmaceutically-acceptable cations, the identities of which are well-known in the art, have been compiled in P. Heinrich Stahl and Camille G. Wermuth, Handbook of Pharmaceutical Salts: Properties, Selection and Use. International Union of Pure and Applied Chemistry, Wiley-VCH 2002, and L. D. Bighley, S. M. Berge, D. C. Monkhouse, in "Encyclopedia of Pharmaceutical Technology". Eds. J. Swarbrick and J. C. Boylan, Vol. 13, Marcel Dekker, Inc., New York, Basel, Hong Kong 1995, pp. 453-499.

In some aspects, the compound is not the dimer disclosed in U.S. patent application Ser. No. 12/577,089 (filed Oct. 9, 2009) having the following structure or a pharmaceutically acceptable salt of the dimer wherein $R^1a$ and $R^1b$ are independently selected from H and F, provided that at least one of $R^1a$ and $R^1b$ is F, Het is an optionally-substituted five- or six-membered heterocycle comprising at least one N, O, or S atom, such as tetrazolyl or oxadiazolyl.

In some aspects, the compound is not the dimer disclosed in U.S. patent application Ser. No. 12/699,864 (filed Feb. 3, 2010), i.e., Compounds of Formula IV can be prepared by a variety of methods, including phosphorylation of an active metabolite of an oxazolidinone-containing antibiotic, such as the compound of Formula I. When the phosphorylation reaction is conducted with two or more equivalents of the active metabolite such as the Formula I compound, formation of the bis-esters such as Formula III is favored. However, in some embodiments, the bis-esters are ineffective antibiotic agents, thus showing that not all phosphate-containing compounds are effective. Therefore, in some embodiments, less than two equivalents of the active metabolite such as Formula I compound are used. Phosphorylation methods typically involve use of an electrophilic phosphorus(V) compound, such as phosphorus oxychloride, $POCl_3$, or a phosphate in the presence of a dehydrating agents, such as a carbodiimide, but other methods can be used. For example, the compounds of Formula IV can be prepared by transesterification of a phosphate-containing ester such as a diphosphate ester with an active metabolite such as the compound of Formula I. Such transesterification reactions are well-known. Similarly, compounds of Formula IV can be prepared in high yield from oxazolidinone-containing phosphates, such as a monophosphate of Formula II by treatment with a dehydrating agent such as carbonyldiimidazole (CDI).

In some embodiments, compounds of Formula IV have utility as water soluble prodrugs of antibacterial agents of oxazolidinone-containing antibiotics, such as Formula I. In some embodiments, Formula IV phosphate dimers have a longer half life in vivo than the oxazolidinone-containing phosphates, such as the monophosphate of Formula II. Consequently, in some embodiments compounds of Formula IV release the active metabolite (e.g., Formula I) over a longer period, which extends the in vivo half-life of the antibacterial agent. Longer biological half-life increases the time the active compound remains above the minimum inhibitory concentration (MIC), and thereby promotes efficacy at a lower drug dose. Longer half-life also reduces the maximum concentration, $C_{max}$, of some embodiments of the antibacterial drug, thereby reducing side-effects in which $C_{max}$ is the pharmacodynamic driver.

Those skilled in the art will appreciate that a variety of prodrugs, salts, hydrates, solvates, and polymorphs can be produced from the compounds disclosed here, and that various isotopically-substituted variants (through, e.g., substitution of deuterium for hydrogen, $^{13}C$ for carbon, $^{15}N$ for nitrogen, or $^{32}P$ for phosphorus) can also be readily produced. All such derivatives are contemplated within the scope of this disclosure.

In another aspect, the present disclosure relates to a pharmaceutical composition comprising one or more physiologically acceptable surface active agents, additional carriers, diluents, excipients, smoothing agents, suspension agents, film forming substances, and coating assistants, or a combination thereof; and a composition disclosed herein. Acceptable additional carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, microcrystalline cellulose, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound disclosed herein with other chemical components, such as diluents or additional carriers. The pharmaceutical composition facilitates administration of the compound to an organism. Multiple techniques of administering a pharmaceutical composition exist in the art including, but not limited to, oral, injection, aerosol, parenteral, and topical administration. Pharmaceutical compositions can also be obtained by reacting the free acid dihydrogen phosphate with inorganic or organic bases such as sodium hydroxide or magnesium hydroxide. In some embodiments, pharmaceutically acceptable salts of the compounds disclosed herein (e.g., as made in situ during the manufacture of an intravenous formulation) are provided.

The term "carrier" refers to a chemical compound that facilitates the incorporation of a compound into cells or tissues.

The term "diluent" refers to chemical compounds diluted in water that will dissolve the composition of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound. As used herein, an "excipient" refers to an inert substance that is added to a composition to provide, without limitation, bulk, consistency, stability, binding ability, lubrication, disintegrating ability, etc., to the composition. A "diluent" is a type of excipient.

The term "physiologically acceptable" refers to a carrier or diluent that does not abrogate the biological activity and properties of the compound.

The pharmaceutical compounds described herein can be administered to a human patient per se, or in pharmaceutical compositions where they are mixed with other active ingredients, as in combination therapy, or suitable carriers or excipient(s). In some embodiments, a dosage form includes those forms in which the compound is admistered per se. In addition, a dosage form may include a pharmaceutical composition. In any case, the dosage form may comprise a sufficient amount of the dimer compound to treat a bacterial infection as part of a particular administration protocol, as would be understood by those of skill in the art. Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compound can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions may be formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, diluents, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the composition can be formulated readily by combining the compositions of interest with pharmaceutically acceptable carriers well known in the art. Such carriers, which may be used in addition to the cationic polymeric carrier, enable the compositions of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP), e.g., Povidone. If desired, disintegrating agents may be added, such as the cross-linked polyvinylpyrrolidone (e.g. Crospovidone), agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in a conventional manner.

For administration by inhalation, the composition can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compositions may also be formulated in rectal compositions such as suppositories or retention enemas, e.g., containing conventional suppository bases such as cocoa butter or other glycerides.

In addition to the formulations described previously, the compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Methods for treating bacterial infections may include administering a therapeutically effective amount of the therapeutic compounds as described herein. Treating a bacterial infection may also include prophylactically administering the therapeutic compounds to prevent infection or the spread of an infection in a subject at imminent risk of infection, such as a subject receiving or about to undergo surgery, an immunocompromised subject, or subject otherwise at risk of an infection if the compound was not administered. The compounds show inhibitory activity against a broad spectrum of bacteria, against methicillin resistant *Staphylococcus aureus* (MRSA) and vancomycin resistant *Enterococci* (VRE) and have excellent relative antibiotic activity with a relatively low concentration thereof or in vivo. Further, the compounds of the present invention may exert potent antibacterial activity versus various human and animal pathogens, including Gram-positive bacteria such as *Staphylococci, Enterococci* and *Streptococci*, anaerobic microorganisms such as *Bacteroides* and *Clostridia*, and acid-resistant microorganisms such as *Mycobacterium* tuberculosis and *Mycobacterium avium*. In an embodiment, the bacterial infection that may be treated or ameliorated is MRSA.

The compositions or pharmaceutical compositions described herein may be administered to the subject by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; as well as (d) administration topically; as deemed appropriate by those of skill in the art for bringing the active compound into contact with living tissue.

Pharmaceutical compositions suitable for administration include compositions where the active ingredients are contained in an amount effective to achieve its intended purpose. In some embodiments, a therapeutically effective amount of a compound is an amount effective to treat a bacterial infection, for example, in a mamalian subject (e.g., a human). The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved adverse side effects disappear. The dosage may range broadly, depending upon the desired effects and the therapeutic indication. Typically, dosages may be about 10 microgram/kg to about 100 mg/kg body weight, preferably about 100 microgram/kg to about 10 mg/kg body weight. Alternatively dosages may be based and calculated upon the surface area of the patient, as understood by those of skill in the art.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). In some embodiments, the dose range of the composition administered to the patient can be from about 0.5 to about 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are about 0.1% to about 500%, more preferably about 25% to about 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of about 0.1 mg to 2000 mg of the active ingredient, preferably about 1 mg to about 500 mg, e.g. 5 to 200 mg. In other embodiments, an intravenous, subcutaneous, or intramuscular dose of the active ingredient of about 0.01 mg to about 100 mg, preferably about 0.1 mg to about 60 mg, e.g. about 1 to about 40 mg is used. In cases of administration of a pharmaceutically acceptable salt, dosages may be calculated as the free acid. In some embodiments, the composition is administered 1 to 4 times per day. Alternatively the compositions of the invention may be administered by continuous intravenous infusion, preferably at a dose of up to about 1000 mg per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the antibiotic effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered may be dependent on the subject being treated, on the subject's weight, the severity of the infection, the manner of administration and the judgment of the prescribing physician.

Compositions disclosed herein can be evaluated for efficacy and toxicity using known methods. For example, the toxicology of the compound may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

In some embodiments, in the pharmaceutical industry, it standard practice to provide substantially pure material when formulating pharmaceutical compositions. Therefore, in some embodiments, "substantially pure" refers to the amount of purity required for formulating pharmaceuticals, which may include, for example, a small amount of amorphous material or other material, wherein the material may still achieve sufficient pourability, lack of hygroscopicity, and purity suitable for pharmaceutical use. In some embodiments, the substantially pure compound contains at least about 96% of the compound by weight, such as at least about 96.1%, 96.2%, 96.3%, 96.4%, 96.5%, 96.6%, 96.7%, 96.8%, 96.9%, 97%, 97.1%, 97.2%, 97.3%, 97.4%, 97.5%, 97.6%, 97.7%, 97.8%, 97.9%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% of the compound.

The terms "approximately, "about," and "substantially" as used herein represent an amount close to the stated amount that still performs the desired function or achieves the desired result. For example, the terms "approximately," "about" and "substantially" may refer to an amount that is within less than 10% of, within less than 5% of, within less than 1% of, within less than 0.1% of, and within less than 0.01% of the stated amount.

EXAMPLES

Example 1

Preparation of the Phosphate Monohydrogen Diester, Formula III

In this and the following Examples, "Formula III" refers to a compound wherein Z is and M=OH.

A 1-L, three-neck round-bottom flask equipped with a magnetic stirrer, nitrogen inlet/outlet and thermocouple was charged with the compound of Formula Ia below (16.0 g, 0.0499 mol], THF (320 mL, 20 vol) and Et$_3$N (21.9 g, 0.216 mol, 5.0 equiv.).

Formula Ia

POCl$_3$ (3.31 g, 0.0216 mol, 0.5 equiv.) was added dropwise via syringe over 5 minutes. The reaction temperature was maintained below 25° C. The batch was aged for 16 hours at room temperature at which point HPLC analysis (XBridge, C18) indicated that the reaction was complete. The reaction vessel was then immersed in an ice-water bath and a 500-mL addition funnel charged with 320 mL of H$_2$O was attached to the reaction vessel. When the temperature of the reaction reached 2.7° C., H$_2$O was added drop wise over 30 minutes. The temperature of the reaction was maintained below 10° C. Upon completion of the H$_2$O addition, the ice-water bath was removed and the batch was aged for 3 hours. The solution was transferred to a 2-L round-bottom flask and concentrated under reduced pressure on a rotary evaporator. After removal of most of the THF from the solution, the aqueous mixture was extracted with 5 1-L portions of CH$_2$Cl$_2$:MeOH (9:1). The CH$_2$Cl$_2$ layers were combined and concentrated to a dark oil. This crude material was purified on 200 g of silica gel, eluting with 10% MeOH/CH$_2$Cl$_2$ to 20% 2 N NH$_3$ in MeOH/CH$_2$Cl$_2$. Fractions containing mostly the bis-ester (as judged by TLC Rf=0.3 eluting with 20% 2 N NH$_3$ in MeOH/CH$_2$Cl$_2$) were combined and concentrated under reduced pressure on a rotary evaporator, during which time a white precipitate was observed. The flask containing the slurry was removed from the rotary evaporator and equipped with a magnetic stir bar and allowed to stir while cooling to room temperature over 3 hours, during which time the slurry thickened. The solid was filtered and dried in a vacuum oven at 45° C. for 16 hours to give 3.55 g of bis-ester as an off-white solid (20% yield). HPLC analysis (Method A): 99.0% (AUC), tR=16.3 min. This reaction was repeated and the combined lots of the compound of Formula III (6.7 g) were slurried in 100 mL of MeOH (15 vol). The slurry was heated to 40° C. for 30 minutes and then allowed to cool to room temperature over 1 hour. The off-white solid was filtered and dried in a vacuum oven at 40° C. for 16 hours to give 6.15 g of the compound of Formula III (92% yield). The $^1$H NMR analysis of the product was consistent with the assigned structure. HPLC analysis (Method A): 99.0% (AUC), tR=16.3 min.

Example 2

Preparation of the Diphosphate Dihydrogen Diester, Formula IV

In Examples 2-5, "Formula IV" refers to a compound wherein Z is n=0 and M=O-imidazolium salt.

A 250-mL 3-neck round-bottom flask equipped with a magnetic stirrer, nitrogen inlet/outlet and thermocouple was charged with the compound of Formula IIa below (5.0 g, 11.1 mmol), carbonyldiimidazole (890 mg, 5.55 mmol, 0.5 equiv.) and DMF (100 mL, 20 vol).

Formula IIa

The suspension was heated to 50° C. and held at that temperature for 4 hours at which point HPLC analysis (XBridge, C18) indicated that the reaction was complete. The reaction was filtered at 50° C. and dried in a vacuum oven at 50° C. for 24 hours to give 5.15 g of the imidazolium salt (i.e., the compound of Formula IV) as an off-white solid (98% yield). The $^1$H NMR analysis of the product was consistent with the assigned structure. HPLC analysis (Method A): 94.5% (AUC), tR=14.6 min.

TABLE 1

| Method A (Waters XBridge C18 Column) | | | |
|---|---|---|---|
| Time (min) | Flow (mL/min) | % A | % B |
| 0.0 | 1.0 | 98.0 | 2.0 |
| 15.0 | 1.0 | 5.0 | 95.0 |
| 25.0 | 1.0 | 5.0 | 95.0 |
| 27.0 | 1.0 | 98.0 | 2.0 |
| 30.0 | 1.0 | 98.0 | 2.0 |

A = 87% 25 mM ammonium bicarbonate solution in water/13% Acetonitrile
B = Acetonitrile
Wavelength = 300 nm

Example 3

Pharmacokinetic Determinations

Figure 1:
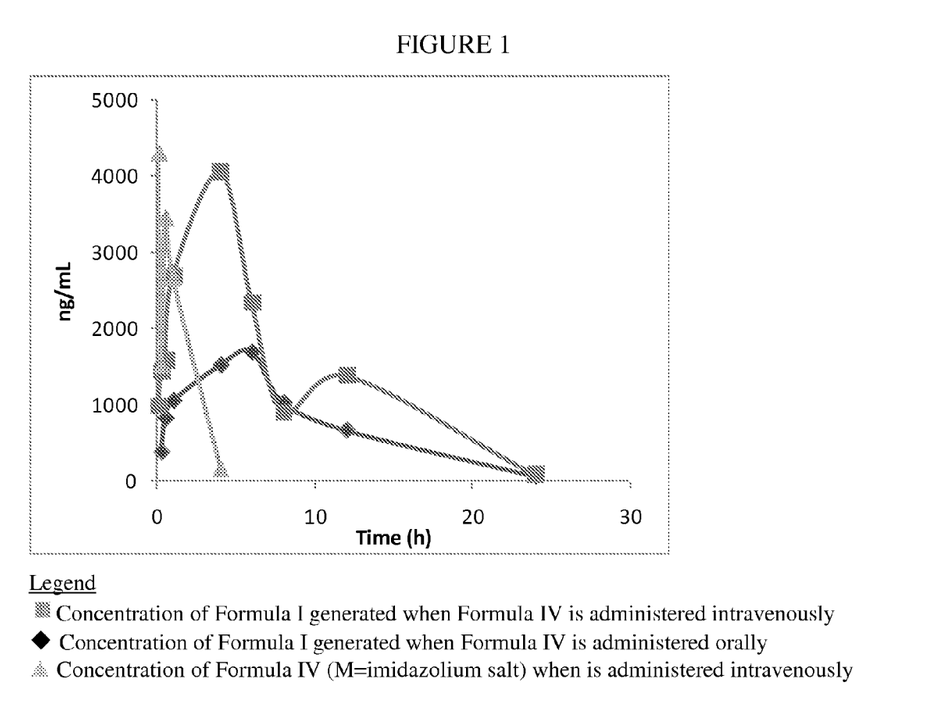
FIG. 1 shows a plot of the pharmacokinetics of a Formula IV compound (as illustrated in Example 2) when administered either orally or intravenously showing both the concentration of the prodrug Formula IV or the active antibacterial agent of Formula Ia.
Figure 2:
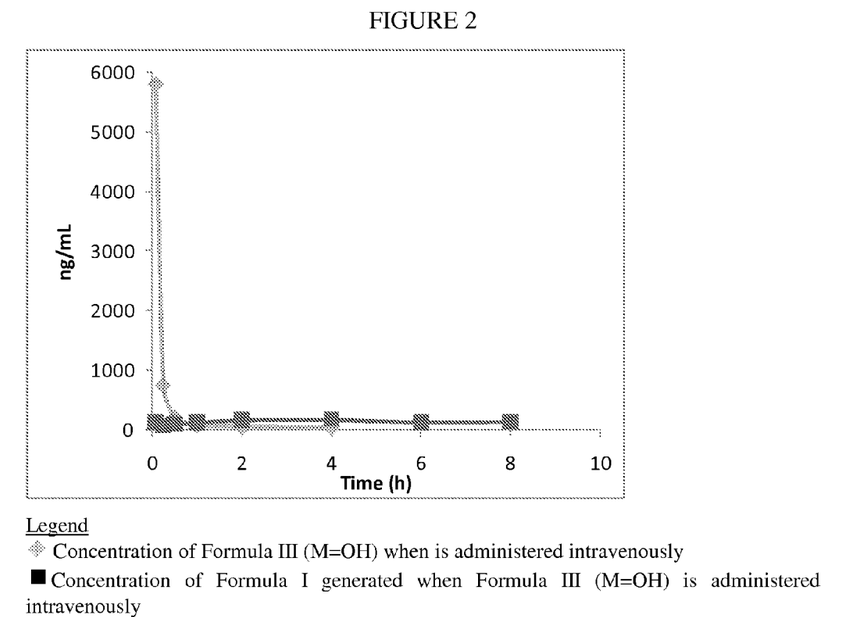
FIG. 2 shows a plot of the pharmacokinetics of a Formula III compound (as illustrated in Example 1) when administered intravenously showing both the concentration of the prodrug Formula III and the active antibacterial agent Formula Ia.
Figure 3:
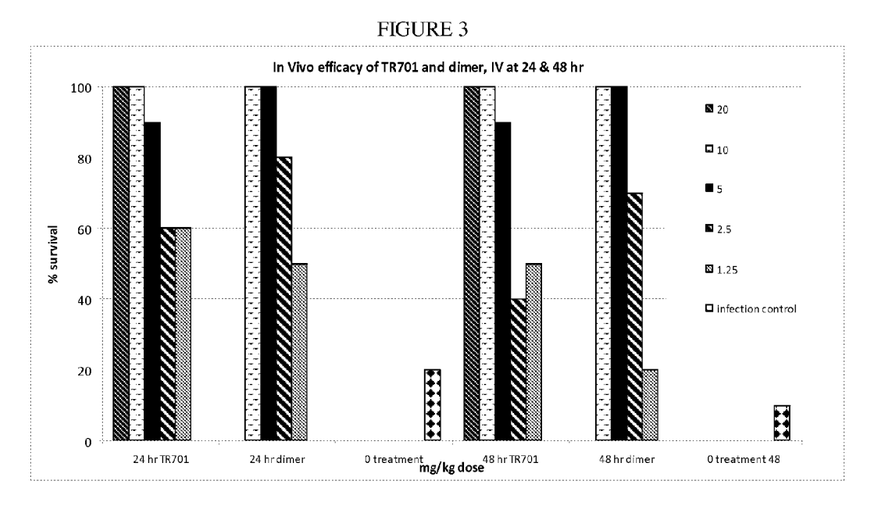
FIG. 3 charts the in vivo efficacy of TR-701 and the dimer Formula IV at 24 and 48 hour intervals at various dosage levels in accordance with Example 5.
Figure 4:
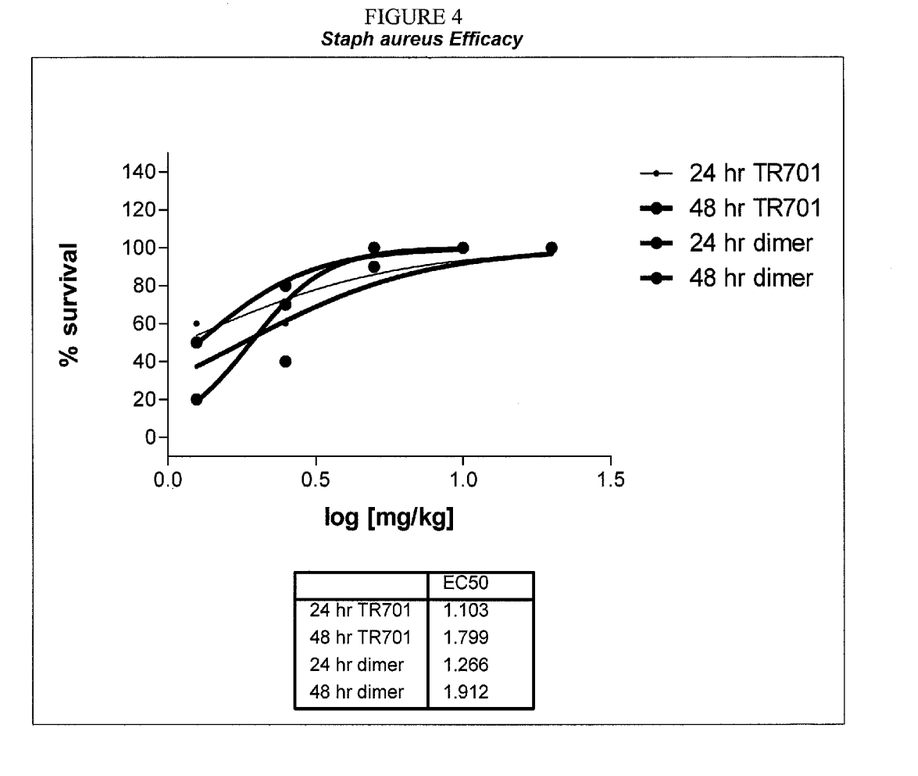
FIG. 4 shows a graph of the *Staphylococcus aureus* in vivo efficacy of TR-701 and the dimer Formula IV at 24 and 48 hour intervals in accordance with Example 5.

Balb/c female mice, 6-7 weeks old (~20 g) were randomized into treatment groups of three animals. Pharmacokinetics of each of the test compounds was evaluated. The test compounds (10 mg/kg) were administered via tail vein or orally to study mice. Blood was collected by cardiac puncture at 5 (intravenously-administered compounds only), 15, 30 minutes and 1, 4, 6, 8, 12 and 24 hours (n=3 at each timepoint). Plasma concentration of each of the compounds of Formula Ia, III (as defined in Example 1), and IV (as defined in Example 2) was analyzed through use of a validated HPLC/UV method. Data are plotted in FIG. 1 and FIG. 2.)

TABLE 2

Summary of pharmacokinetic data for both the prodrug and active component when the prodrugs of Formula IV (as defined in Example 2) and Formula III (as defined in Example 1) are dosed in mice.

| Compound Dosed | Compd. Measured | Rsq | $\tau_{1/2}$ (h) | $T_{max}$ (h) | $C_{max}$ (µg/ml) | $AUC_{0-24 h}$ (µg hr/ml) | $Vz_{obs}$ (L/kg) | $CL_{obs}$ (L/hr/kg) |
|---|---|---|---|---|---|---|---|---|
| intravenous Formula IV 10 mg/kg | Formula IV | 1.00 | 0.77 | 0.08 | 4.30 | 7.00 | 1.53 | 1.39 |
| intravenous Formula IV 10 mg/kg | Formula Ia | 0.97 | 3.74 | 4.00 | 4.06 | 36.40 | 1.46 | 0.27 |
| Oral Formula IV 10 mg/kg | Formula Ia | 0.99 | 3.89 | 6.00 | 1.70 | 18.3 | 3.01 | 0.54 |
| intravenous Formula III 10 mg/kg | Formula III | 0.93 | 3.05 | 0.08 | 5.79 | 1.14 | 33.43 | 7.61 |
| intravenous Formula III 10 mg/kg | Formula Ia | 0.58 | 12.04 | 4.00 | 0.17 | 1.16 | 48.65 | 2.80 |

TABLE 3

Pharmacokinetic data for both the prodrug parent Formula IV (as defined in Example 2) and the active antibacterial agent Formula Ia when prodrug Formula IV is given either orally or intravenously at 10 mg/kg (all concentrations in ng/ml).

| Time (hr) | Oral route Formula Ia conc. | Oral route Formula IV conc. | Intravenous route Formula Ia conc. | Intravenous route Formula IV conc. |
|---|---|---|---|---|
| 0.08 | ND | ND | 984.41 | 4300 |
| 0.25 | 381.22 | ND | 1439.02 | 1515 |
| 0.5 | 821.29 | ND | 1588.67 | 3450 |
| 1 | 1053.56 | ND | 2692.21 | 2661 |
| 4 | 1520.58 | ND | 4059.94 | 157 |
| 6 | 1697.18 | ND | 2341.86 | ND |
| 8 | 1029.09 | ND | 896.47 | ND |
| 12 | 667.74 | ND | 1385.48 | ND |
| 24 | 65.26 | ND | 84.06 | ND |

ND: Not Detected because amount of compound is below limits of detection

TABLE 4

Pharmacokinetic data for both the prodrug parent Formula III
(as defined in Example 1) and the active antibacterial agent
Formula Ia when prodrug Formula III (as defined in Example 1)
is given intravenously at 10 mg/kg (all concentrations in ng/ml).

| Time (hr) | Intravenous route Formula III conc. | Intravenous route Formula Ia conc. |
|---|---|---|
| 0.08 | 5794.47 | 124.18 |
| 0.25 | 749.02 | 78.46 |
| 0.5 | 210.06 | 90.85 |
| 1 | 81.05 | 123.76 |
| 2 | 53.78 | 167.77 |
| 4 | 39.49 | 174.61 |
| 6 | ND | 131.45 |
| 8 | ND | 138.71 |

ND: Not Detected because amount of compound is below limits of detection

Example 4

Minimum Inhibitory Concentration Determinations

Minimum inhibitory concentrations were determined by broth microdilution according to Clinical and Laboratory Standards Institute (CLSI) approved methods (M7-A7) and interpreted using Alamar Blue to visualize cell viability. Dilutions of each of the compounds of the compounds were tested against *S. aureus* Smith strain or *S. aureus* plus 20% mouse serum.

TABLE 5

MIC results (in µg/ml)

|  | *S. aureus* Smith | *S. aureus* Smith + 20% mouse serum |
|---|---|---|
| Formula IIb (TR-701) | >64 | 4 |
| Formula III (as defined in Example 1) | >64 | >64 |
| Formula IV (as defined in Example 2) | >64 | 32 |

Example 5

Efficacy Testing: Mouse Septicemia Model

Balb/c female mice, 6-7 weeks old (~20 g) were randomized into treatment groups of 10 animals. Staphylococcus aureus Smith strain ATCC #13709 was cultured overnight in BHI medium at 37° C. Cells were back-diluted 1:10 and allowed to grow for 5 hours. The inoculum used for infecting mice was prepared by diluting the culture in 5% Hog Gastric Mucin/PBS to a concentration of $1 \times 10^6$ cfu/ml. 100 µl of culture/mucin was reserved to quantify the starting cfu/ml by serial diluting and plating the culture. Mice were infected with 500 µl of the inoculum just prior to drug dosing. The drugs were dosed within 15 minutes of infection.

Mice received intravenous doses of each of the test compounds at the concentrations described in Tables 6 and 7, based on calculated average weight of all the mice (~20 g). Forty-eight hours post-infection, the number of surviving mice was determined.

TABLE 6

Survival of Balb/c Mice, female, intravenous administration, 200 µL
dosage of Formual III (as defined in Example 1),
10 mice were treated in each group.

| Group | Treatment | Concentration mg/kg | Concentration mg/m² | 48 hr survival |
|---|---|---|---|---|
| 1 | Formula III | 10 | 0.2 | 1/10 |
| 2 | Formula III | 5 | 0.1 | 1/10 |
| 3 | Formula III | 2.5 | 0.05 | 0/10 |
| 4 | Formula III | 1.25 | 0.025 | 1/10 |
| 5 | infection control | — |  | 1/10 |

The data in Table 6 indicate that Formula III is ineffective as an antibiotic because the survival rates are similar to the infection control, thus showing that not all phosphate-containing compounds are effective.

TABLE 7

Survival of Balb/c Mice, female, intravenous administration
of Formula IV (as defined in Example 2), 200 µL
dosage, 10 mice were treated in each group.

| Group | Treatment | Concentration mg/kg | Concentration mg/m² | 24 hr survival | 48 hr survival |
|---|---|---|---|---|---|
| 1 | Formula IV | 10 | 0.2 | 10/10 | 10/10 |
| 2 | Formula IV | 5 | 0.1 | 10/10 | 10/10 |
| 3 | Formula IV | 2.5 | 0.05 | 8/10 | 7/10 |
| 4 | Formula IV | 1.25 | 0.025 | 5/10 | 2/10 |
| 5 | infection control | — |  | 2/10 | 1/10 |

The data in Table 7 show 100% (i.e.,10/10) survival rate after 24 and 48 hour intervals at dosages of 10 and 5 mg/kg. Without being bound by theory, it appears that the presence of an additional phosphate in Formula IV increases the space between the Z moieties in comparison to Formula III allowing a phosphatase to cleave the phosphate more readily. Thus, it is expected that the presence of additional phosphate groups between Z moieties would act similarly as the diphosphate.

TABLE 8

Comparison of Survival of Balb/c Mice, female, intravenous
administration of Formula IV (as defined in Example 2)
and the disodium phosphate salt of Formula Ia (TR-701),
200 µL dosage, 10 mice were treated in each group.

| Concentration mg/kg | % Survival-10 mice per group | | | | | infection control |
|---|---|---|---|---|---|---|
|  | 20 | 10 | 5 | 2.5 | 1.25 |  |
| 24 hr TR701 | 100 | 100 | 90 | 60 | 60 |  |
| 24 hr dimer |  | 100 | 100 | 80 | 50 |  |
| 0 treatment |  |  |  |  |  | 20 |
| 48 hr TR701 | 100 | 100 | 90 | 40 | 50 |  |
| 48 hr dimer |  | 100 | 100 | 70 | 20 |  |
| 0 treatment 48 |  |  |  |  |  | 10 |

The same procedure was used as in Example 5's Efficacy Testing description. The data in Table 8 show that survival rates were surprisingly increased by the intravenous administration of Formula IV (as defined in Example 2) in comparison to TR-701 (the disodium phosphate salt of Formula Ia) at dosages of 5 and 2.5 mg/kg as shown in Table 8.

What is claimed is:

1. A pharmaceutical composition comprising a therapeutically effective amount of a compound having the following structure wherein each Z is wherein * is the point of attachment of Z to P;
wherein M OR$_1$;
wherein R1 is H or a pharmaceutically acceptable cation.

2. The pharmaceutical composition of claim 1, wherein the pharmaceutically acceptable cation is a sodium cation.

3. The pharmaceutical composition of claim 1, wherein each Z is

4. The pharmaceutical composition of claim 1, further comprising a pharmaceutically acceptable carrier, diluent or excipient.

5. The pharmaceutical composition of claim 2, wherein the structure is:

or the sodium salt thereof.

6. A method of preparing the compound in the pharmaceutical composition of claim 1, comprising the step of treating a compound of the formula Z—H with a phosphorylating agent.

7. A method of preparing the compound in the pharmaceutical composition of claim 1, comprising the step of treating with a dehydrating agent the compound Z—P', wherein P' is a mono-or dihydrogen phosphate group.

8. The method of claim 6, wherein the phosphorylating agent is POCl$_3$.

9. A method of treating a bacterial infection comprising administering the pharmaceutical composition of claim 1 to a subject in need thereof.

10. A method of treating a bacterial infection comprising administering the pharmaceutical composition of claim 2 to a subject in need thereof.

11. A method of treating a bacterial infection comprising administering the pharmaceutical composition of claim 4 to a subject in need thereof.

12. A method of treating a bacterial infection comprising administering the pharmaceutical composition of claim 5 to a subject in need thereof.

13. The pharmaceutical composition of claim 2, further comprising a pharmaceutically acceptable carrier, diluent or excipient.

14. The pharmaceutical composition of claim 5, further comprising a pharmaceutically acceptable carrier, diluent or excipient.

* * * * *

UNITED STATES PATENT AND TRADEMARK OFFICE
CERTIFICATE OF CORRECTION

PATENT NO.        : 8,580,767 B2                    Page 1 of 1
APPLICATION NO.   : 12/787293
DATED             : November 12, 2013
INVENTOR(S)       : Hester, II et al.

It is certified that error appears in the above-identified patent and that said Letters Patent is hereby corrected as shown below:

On the Title Page

In column 2 (page 2, item 56) at line 40, Under Other Publications, change "Pharh4aceutical" to --Pharmaceutical--.

In column 1 (page 3, item 56) at line 16, Under Other Publications, change "opinionand" to --opinion and--.

In the Specification

In column 7 at line 20, Change "wherein" to --wherein *--.

In column 7 at line 47, Change "$N_1Z_1R_2$;" to --$NR_1R_2$;--.

In column 9 at line 34, Change "F," to --F.--. (2nd occurrence)

In column 11 at line 62, Change "admistered" to --administered--.

In column 15 at line 11, Change "mamalian" to --mammalian--.

In column 22 at line 4, Change "Formual" to --Formula--.

Signed and Sealed this
Third Day of June, 2014

Michelle K. Lee
*Deputy Director of the United States Patent and Trademark Office*

UNITED STATES PATENT AND TRADEMARK OFFICE
Certificate

Patent No. 8,580,767 B2                                                                        Patented: November 12, 2013

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: D. Keith Hester, II, Delmar, NY (US); Robert J. Duguid, Glenmont, NY (US); John Finn, Encinitas, CA (US); and Douglas Phillipson, Del Mar, CA (US).

Signed and Sealed this Twenty-fifth Day of November 2014.

SREENI PADMANABHAN
*Supervisory Patent Examiner*
Art Unit 1627
Technology Center 1600